US010913985B2

(12) United States Patent
Jamnikar et al.

(10) Patent No.: US 10,913,985 B2
(45) Date of Patent: Feb. 9, 2021

(54) PREDICTING PRODUCTIVITY IN EARLY CELL LINE DEVELOPMENT

(71) Applicant: Lek Pharmaceuticals d.d., Ljubljana (SI)

(72) Inventors: Uroš Jamnikar, Menges (SI); Marjanca Blas, Menges (SI); Kristina Gruden, Ljubljana (SI)

(73) Assignee: Lek Pharmaceuticals d.d., Ljubljana (SI)

( * ) Notice: Subject to any disclaimer, the term of this patent is extended or adjusted under 35 U.S.C. 154(b) by 308 days.

(21) Appl. No.: 15/525,324

(22) PCT Filed: Nov. 12, 2015

(86) PCT No.: PCT/EP2015/076391
§ 371 (c)(1),
(2) Date: May 9, 2017

(87) PCT Pub. No.: WO2016/075217
PCT Pub. Date: May 19, 2016

(65) Prior Publication Data
US 2017/0321288 A1 Nov. 9, 2017

(30) Foreign Application Priority Data

Nov. 12, 2014 (EP) .................................... 14192810

(51) Int. Cl.
| | |
|---|---|
| *C12Q 1/6888* | (2018.01) |
| *C12N 15/67* | (2006.01) |
| *C07K 16/00* | (2006.01) |
| *C12N 5/071* | (2010.01) |
| *C12P 21/00* | (2006.01) |

(52) U.S. Cl.
CPC ............ *C12Q 1/6888* (2013.01); *C07K 16/00* (2013.01); *C12N 5/0682* (2013.01); *C12N 15/67* (2013.01); *C12P 21/00* (2013.01); *C07K 2317/14* (2013.01); *C07K 2317/51* (2013.01); *C07K 2317/515* (2013.01); *C12N 2510/02* (2013.01); *C12Q 2600/158* (2013.01)

(58) Field of Classification Search
None
See application file for complete search history.

(56) References Cited

U.S. PATENT DOCUMENTS

2013/0302816 A1* 11/2013 Obrstar .................. C12N 15/67
435/6.17

FOREIGN PATENT DOCUMENTS

| WO | 2006014899 A2 | 2/2006 |
|---|---|---|
| WO | 2010007388 A1 | 1/2010 |
| WO | 2010130800 A1 | 11/2010 |
| WO | 2013156458 A1 | 10/2013 |

OTHER PUBLICATIONS

Maccani et al. Identification of microRNAs specific for high producer CHO cell lines using steady-state cultivation. Published online Jul. 23, 2014. Appl. Microbiol. Biotechnol. vol. 98, p. 7535-7548. (Year: 2014).*
Jiang et al. Regulation of Recombinant Monoclonal Antibody Production in Chinese Hamster Ovary Cells: A Comparative Study of Gene Copy Number, mRNA Level, and Protein Expression. Published on Web Nov. 15, 2005. Biotechnology Progress. vol. 22, pp. 313-318. (Year: 2005).*
International Search Report and Written Opinion for PCT/EP2015/076391, 16 pages.
Ong, Derrick Sek Tong, et al., FKBP10 Depletion Enhances Glucocerebrosidase Proteostasis in Gaucher Disease Fibroblasts, Chemistry & Biology, Mar. 21, 2013, pp. 403-415.
Winterstein, D., et al., Down Regulation of FKBP65 during transmformation and its association with the ras-raf signaling pathway, Proceedings of the American Association for Cancer Research Annual Meeting, vol. 37, No. 0, 1996, p. 503.
Fairbank, Maria, et al., Ring finger palmitoylation of the endoplasmic reticulum Gp78 E3 ubiquitin ligase, FEBS Letters 586, 2012, pp. 2488-2493.
Clarke, Colin, et al., Predicting cell-specific productivity from CHO gene expression, Journal of Biotechnology, 2011, 151, pp. 159-165.
Edros, Raihana Z, et al., Using Molecular Markers to Characterize Productivity in Chinese Hamster Ovary Cell Lines, School of Chemical and Bioprocess Engineering and Conway Institute of Biomolecular and Biomedical Research, Oct. 17, 2013.

* cited by examiner

*Primary Examiner* — Channing S Mahatan
(74) *Attorney, Agent, or Firm* — Luedeka Neely Group, P.C.

(57) ABSTRACT

The present invention relates in general to the field of recombinant protein expression. In particular, the present invention relates to a method for selecting a suitable candidate cell clone for recombinant protein expression and to a host cell for recombinant protein expression, the host cell exhibiting artificially modified gene expression of at least one gene selected from the group consisting of: Fkbp10, ZdhhC6, Myrip, Actc1, AC124993.19, Runx2, AC158560.4, PlekhB1, Rps6KA2, Sept1, Sprr2k, and Flt1.

12 Claims, 1 Drawing Sheet
Specification includes a Sequence Listing.

PREDICTING PRODUCTIVITY IN EARLY CELL LINE DEVELOPMENT

This application is a Section 371 national phase entry of PCT application PCT/EP2015/076391, filed Nov. 12, 2015. This application also claims the benefit of the earlier filing date of European patent application 14192810.1, filed Nov. 12, 2014.

This application contains a Sequence Listing which has been submitted electronically in ASCII format and is herein incorporated by reference. The ASCII file, created on Mar. 13, 2017, is named 72600us-temp-20170313-HEX-007 PCT_ST25.txt, and is 5,784 bytes in size.

The present invention relates in general to the field of recombinant protein expression. In particular, the present invention relates to a method for selecting a suitable candidate cell clone for recombinant protein expression and to a host cell for recombinant protein expression, the host cell exhibiting artificially modified gene expression of at least one gene selected from the group consisting of: Fkbp10, ZdhhC6, Myrip, Actc1, AC124993.19, Runx2, AC158560.4, PlekhB1, Rps6KA2, Sept1, Sprr2k, and Flt1.

Recombinant production of recombinant proteins has become an important factor in modem biotechnology. Chinese hamster ovary (CHO) cells have become in many cases the host of choice because of their capacity for proper protein folding, assembly, and posttranslational modification. Moreover CHO cell lines have been well characterized and their history of regulatory approval for recombinant proteins produced from these cell lines is very well known.

One of the most important requirements for a recombinant host cell is high productivity. However, in the process of establishing cell lines expressing a particular recombinant protein, productivity of the resulting clones may vary significantly and can usually be assessed only after empirically testing cell lines for productivity. Consequently, this requires culturing numerous clones over extended periods of time (up to several months) prior to actual selection of cell lines for the production purposes.

Many publications in the art are focused on transcriptome analysis of differentially expressed genes in CHO cells under stressful conditions, including hyperosmotic media, low temperature, and sodium butyrate treatment, that are all known to increase productivity.

An interesting approach was described by Clarke and colleagues (Clarke, C., et al., J Biotechnol, 2011. 151(2): p. 159-65) who presented a predictive model of productivity in CHO bioprocess culture based on gene expression profiles. The dataset used to construct the model consisted of transcriptomic data from stationary phase and temperature-shifted CHO production cell lines and were used to investigate gene expression over a range of high and low monoclonal antibody producing CHO cell lines. Beside development of the model that enables to predict specific productivity (Qp) they prioritized some genes for future studies.

Edros and colleagues (Edros, R. Z. et al., PLoS One, 2013. 8(10): p. e75935) studied the identification of candidate determinants of high productivity by profiling the molecular and morphological characteristics of CHO cell lines. The study revealed that, overall, heavy chain mRNA had the strongest association with specific productivity followed by light chain mRNA, heavy chain intracellular polypeptides and intracellular antibodies. A significant correlation was also obtained between specific productivity and molecular markers as growth rate, biomass, endoplasmic reticulum, and light chain polypeptides.

However, there is still an immense need in the art for a means allowing fast identification of suitable, preferably highly productive, candidate cell clones under standard cell culture conditions early on in cell line development to avoid the need of long term cultivation and respective costs in terms of time and money.

Thus, the problem to be solved by the present invention was to provide a means allowing identification of suitable, preferably highly productive, candidate cell clones under standard cell culture conditions early on in cell line development. The inventors have solved said problem by way of the subject-matter set forth in the appended claims.

In the following a brief description of the appended FIGURE will be given. The FIGURE is intended to illustrate the present invention in more detail. However, it is not intended to limit the subject matter of the invention to any extent.

In a first aspect the present invention relates to a method for selecting a suitable candidate cell clone for recombinant protein expression, the method comprising the steps of:
 a) determining for at least two cell clones, preferably expressing a recombinant protein, the expression level of a gene selected from the group consisting of:
  Fkbp10, ZdhhC6, Myrip, Actc1, AC124993.19, Runx2, AC158560.4, PlekhB1, Rps6KA2, Sept1, Sprr2k, and Flt1, and
 b) selecting out of said at least two cell clones a cell clone for further expansion, whose expression level of said gene is with respect to the expression level of said same gene in at least one other clone tested in step a):
  i) upregulated, if the gene is selected from the group of genes consisting of:
   ZdhhC6, Myrip, Actc1, AC124993.19, and Runx2, or
  ii) downregulated, if the gene is selected from the group of genes consisting of:
   Fkbp10, AC158560.4, PlekhB1, Rps6KA2, Sept1, Sprr2k, and Flt1.

The method according to the present invention allows a selection of a promising cell clone early on in cell line development without the need for long term cultivation and analysis. For this purpose the expression level of at least one gene selected from the group consisting of Fkbp10, ZdhhC6, Myrip, Actc1, AC124993.19, Runx2, AC158560.4, PlekhB1, Rps6KA2, Sept1, Sprr2k, and Fill is determined in step a) of the inventive method. If herein reference is made to determining the "expression level", then in particular the expression level of RNA expression is contemplated. While protein expression may theoretically also be used, said approach will usually be much less efficient. A person skilled in the art is readily familiar with determining expression levels, in particular of RNA. For example, as small aliquot may be removed from the candidate clone sample and quantitative RT-PCR may be used for determination of the respective expression levels. Moreover, determining the "expression level" in the context of the inventive method refers to determining the "expression level" of the endogenous gene(s) only, and not to determining the "expression level" of the same genes if present as transgenes.

Step a) refers to the determination of the expression level in at least two cell clones. Two cell clones are the minimum requirement to allow any comparison in expression level. Already for two clones it will be possible to decide with the method of the present invention, which of the two clones will most likely be the more promising candidate for cell line development. However, usually many more clones will be analysed. For example, the method of the invention may involve determining said expression level for at least 3, 4, 5, 6, 7, 8, 9, 10, 15, 20, 50, 75 or at least 100 candidate clones.

The method of the present invention can be carried out prior to transfection, i.e. the cell clones need not yet express a recombinant protein. In such scenario a pre-selection of a promising cell clone is already made by establishing clones of a given cell line and analysing them with the method of the invention. The selected clone or clones may then be used for transfection etc. Usually however, or even in addition, the expression level of the inventive group of genes is analysed after the host cell has been transfected or transformed and the respective culture has been plated to generate single cell clones. Then, the candidate clones express a recombinant protein. According to the invention, the type of recombinant protein expressed is not of relevance. It may be any type of recombinant protein. The recombinant protein may be for example an antibody, antibody light or heavy chain, a toxin, a cytokine, a growth factor, a growth factor receptor, an enzyme, or a hormone. Preferably, the recombinant protein is an antibody. As the type of recombinant protein expressed is not of particular relevance for the present invention, it is not a prerequisite, although preferred, that the clones (for which the expression level of a particular gene is determined in step a) of the inventive method) express the very same recombinant protein (see also further below). Ideally, they should however preferably at least express the same type of recombinant protein or a recombinant protein of comparable size. In a preferred embodiment of the invention the recombinant protein expressed by said clones is the same type of recombinant protein, such as an antibody.

The method of the present invention may be carried out by determining the expression level of only one gene selected from the group consisting of: Fkbp10, ZdhhC6, Myrip, Actc1, AC124993.19, Runx2, AC158560.4, PlekhB1, Rps6KA2, Sept1, Sprr2k, and Flt1. However, while the invention may be carried out by determining the expression level of only one gene selected from said group, analysis of more than one gene may prove helpful for the selection decision. Thus, in a preferred embodiment, the expression level of more than one gene selected from the group consisting of Fkbp10, ZdhhC6, Myrip, Actc1, AC124993.19, Runx2, AC158560.4, PlekhB1, Rps6KA2, Sept1, Sprr2k, and Flt1 is determined. For example, an inventive method may involve determining the expression level of at least 2, at least 3, at least 4, at least 5, at least 6, at least 7, at least 8, at least 9, at least 10, at least 11 or all 12 genes of said group. It is particularly preferred if the expression level of at least two genes of said group are determined.

In most embodiments of the present invention the expression level will be determined in step a) of the inventive method in parallel for the at least two clones. However, that need not necessarily be the case. For example, there may be a first round of cloning, in which at least one clone is analysed as required by step a). The expression levels determined for said clone (or clones) may then serve for later transfection experiments as reference (the reference clone has still been analysed as required by step a) of the inventive method, albeit at a different point in time). Thus, in some embodiments of the invention, the expression level for said gene or genes are not determined in parallel in step a) for said at least two cell clones. In particular in such scenario it also becomes evident that the recombinant protein expressed by said at least two clones need not be identical (see above). For example, if in a first round of cloning a particular promising (or disappointing) clone for antibody A has been identified, the respective expression levels may serve as reference for later transfection experiments with clones for antibody B (see in this respect also further below the passage on selection of a candidate clone by indirect means). While the expression levels of the cell need not be determined in parallel, the conditions under which the expression levels are determined should of course be preferably identical. For example, step a) is preferably carried out after the same time span after cloning, e.g. within two weeks after cloning (e.g. in the time period of 48 hours to 14 days after cloning, 72 hours to 14 days after cloning, 48 hours to 10 days after cloning, 72 hours to 10 days after cloning, etc.), even more preferably within one week after cloning (e.g. in the time period of 48 hours to 7 days after cloning, 72 hours to 7 days after cloning, 48 hours to 4 days after cloning, 72 hours to 4 days after cloning, etc.). Furthermore, the expression level of said gene or genes is preferably determined for said at least two clones in early log phase (exponential phase) of growth. A person skilled in the art will be familiar with the respective cell culturing techniques and can ascertain said condition, e.g. by appropriate splitting of the cultures and replenishing of fresh media. General culture conditions should preferably be identical, except maybe for necessary deviations, e.g. with respect to antibiotic resistance selection, amplification with MTX etc. It is self-evident, that the cell background (e.g. CHO cell) of the clones analysed in step a) and compared in step b) of the inventive method may not be different.

It is also noted, that step a) of the inventive method is preferably not carried out on cell clones who have been subjected to changes in cultivation parameters, such as temperature shifts, hyperosmotic pressure, sodium butyrate treatment, stress conditions in general, etc. Even more preferably, step a) of the inventive method is carried out with cell clones which have been exposed merely to standard (cell cultivation) conditions for the respective host cell.

The method of the present invention is not limited to a particular type of host cell. The method of the present invention may be applied in principle to any type of host cell. However, in a preferred embodiment of the present invention the cell clones used for the method of the present invention are mammalian cell clones, such as human or rodent cell clones. If the host cell is a mammalian cell, then said mammalian cell is preferably, but not necessarily, not a monkey cell, such as a COS cell. In particular such mammalian host cell is preferably not a monkey cell, such as a COS cell, if the clone is selected for further expansion in view of an upregulated expression level of ZdhhC6. Particularly preferred host cells are CHO cell clones, such as CHO-K1, CHO-SSF3 or CHO-K1PD cell clones, which have been particularly analysed in the present case.

As mentioned previously, in preferred embodiments of the present invention the determining of the expression level in step a) involves quantitative RT-PCR. A person skilled in the art will understand, that the present invention contemplates in particular the specific detection and determination of the expression levels of the specific gene or genes selected from the group consisting of Fkbp10, ZdhhC6, Myrip, Actc1, AC124993.19, Runx2, AC158560.4, PlekhB1, Rps6KA2, Sept1, Sprr2k, and Flt1. Thus, step a) of the method of the present invention does preferably not involve complete transcriptome profiling, at least not for all clones tested.

The sequence of the genes selected from the group consisting of Fkbp10, ZdhhC6, Myrip, Actc1, AC124993.19, Runx2, AC158560.4, PlekhB1, Rps6KA2, Sept1, Sprr2k, and Flt1 are known in the art and are publically available from respective databases. A person skilled in the art will be readily capable to design forward primers, reverse primers and probes in general for these genes and for the respective species of interest. For the Chinese hamster exemplary the gene abbreviation (gene symbol), gene description and Gene ID in the Ensembl database are given in table 1a below. Tables 1b to 1d below provide forward primers, reverse primers and probes used herein.

TABLE 1a

| Gene symbol | Gene Description | Gene ID |
|---|---|---|
| AC158560.4 | Mus musculus chromosome 15, clone RP24-352F5, complete sequence | N.A. |
| PlekhB1 | pleckstrin homology domain containing, family B (evectins) member 1 Gene [Source: MGI Symbol; Acc: MGI: 1351469] | ENSMUSG00000030701 |
| Rps6KA2 | ribosomal protein S6 kinase, polypeptide 2 Gene [Source: MGI Symbol; Acc: MGI: 1342290] | ENSMUSG00000023809 |
| Sept1 | septin 1 Gene [Source: MGI Symbol; Acc: MGI: 1858916] | ENSMUSG00000000486 |
| Sprr2k | small proline-rich protein 2K Gene [Source: MGI Symbol; Acc: MGI: 1330344] | ENSMUSG00000054215 |
| Flt1 | FMS-like tyrosine kinase 1 Gene [Source: MGI Symbol; Acc: MGI: 95558] | ENSMUSG00000029648 |
| Fkbp10 | FK506 binding protein 10 Gene [Source: MGI Symbol; Acc: MGI: 104769] | ENSMUSG00000001555 |
| Actc1 | actin, alpha, cardiac muscle 1 Gene [Source: MGI Symbol; Acc: MGI: 87905] | ENSMUSG00000068614 |
| ZdhhC6 | zinc finger, DHHC domain containing 6 Gene [Source: MGI Symbol; Acc: MGI: 1914230] | ENSMUSG00000024982 |
| Myrip | myosin VIIA and Rab interacting protein Gene [Source: MGI Symbol; Acc: MGI: 2384407] | ENSMUSG00000041794 |
| AC124993.19 | Mus musculus chromosome 15, clone RP23-150J21, complete sequence | N.A. |
| Runx2 | runt related transcription factor 2 Gene [Source: MGI Symbol; Acc: MGI: 99829] | ENSMUSG00000039153 |

TABLE 1b

Forward primer sequences used for the RT-qPCR.

| Gene | Sequence | SEQ ID NO: |
|---|---|---|
| AC158560.4 | GCATTCAATTTAATTTGCCAAGTCAGGAA | 1 |
| PlekhB1 | CCTTCTTCCCACTACTAGCTTCTCT | 2 |
| Rps6KA2 | TGTGCTATCTAATGTTGGCAGTATTGT | 3 |
| Sept1 | CTGCGCCGCATGCAA | 4 |
| Sprr2k | CTCTCATGGATGCCGAAGAATCTT | 5 |
| Flt1 | CTTTGTGCAGTGCCTTGCT | 6 |
| Fkbp10 | GCCTGTTTGAAGACATGGATCTCA | 7 |
| Actc1 | CAGGCCCATCCATTGTCCAT | 8 |
| ZdhhC6 | GCTCTCCTTTGGGTGGAACACC | 9 |
| Myrip | GCCTGTTCTATGGCATTTGAACTTT | 10 |
| AC124993.19 | CGCCCATCTCAGCTTCTTCAA | 11 |
| Runx2 | CTTTTGTTTTTATTTCTTATTTTTCTGATTGCTATTGC | 12 |

TABLE 1c

Reverse primer sequences used for the RT-qPCR.

| Gene | Sequence | SEQ ID NO: |
|---|---|---|
| AC158560.4 | CGCATGGAATTTCAAAAAATTGAAAAGTTGT | 13 |
| PlekhB1 | GCTCACCTGATCCACAGCAA | 14 |

TABLE 1c-continued

Reverse primer sequences used for the RT-qPCR.

| Gene | Sequence | SEQ ID NO: |
|---|---|---|
| Rps6KA2 | TGGCATATTTTCTTCTGTGCTTGAGA | 15 |
| Sept1 | GCCCTGAGCCTGGTTCTG | 16 |
| Sprr2k | CTCATGGAAATGCCTTCCCTAGTAA | 17 |
| Flt1 | TGCCGTCTTCGGGTAATGC | 18 |
| Fkbp10 | GTCCTTTGCCCTCATTCACTTG | 19 |
| Actc1 | GCACAATACCACCATCCTGAATGTA | 20 |
| ZdhhC6 | GAATGGAATGATTGGGAGAGGATCT | 21 |
| Myrip | AAAATAATTTTCTGGAACTATAGCATGTTTATGGTTTAAAT | 22 |
| AC124993.19 | ATGATAAACCTACTCCCCTCTTTCCA | 23 |
| Runx2 | TGACCTGTGGTACAAAGCAGAATTT | 24 |

TABLE 1d

Probe sequences used for the RT-qPCR.

| Gene | Sequence | SEQ ID NO: |
|---|---|---|
| AC158560.4 | CCTCCTGGAACCTCC | 25 |
| PlekhB1 | CAATCCCTGGGTTTCC | 26 |
| Rps6KA2 | CAACGCAGGCATCTTA | 27 |
| Sept1 | CTGAGCTTGCATCTTC | 28 |
| Sprr2k | ACACCCCAAATGCC | 29 |
| Flt1 | CCCCGCCTATACATCA | 30 |
| Fkbp10 | CCCAGAAGAGTTCTCC | 31 |
| Actc1 | CAAGTGCTTCTAAGATGTC | 32 |
| ZdhhC6 | CCGGGCTGCACTCAT | 33 |
| Myrip | CCTTGTGCCAAATAAG | 34 |
| AC124993.19 | CATCTCACAGAAAACTC | 35 |
| Runx2 | CATGGAAAGCAAACCTT | 36 |

Once the relative expression level for the gene or genes has been obtained it should preferably be $\log_2$ transformed, i.e., in preferred embodiments of the invention the expression level is compared and the clone is selected on basis of relative expression values ($\log_2$). The expression values should be normalized based on housekeeping or reference genes (e.g. GAPDH or ACTB, for which the expression is considered to be constant under all conditions) to render the obtained values also comparable between different experiments.

In the inventive method, step b) requires selecting out of said at least two cell clones a cell clone for further expansion, whose expression level of said gene is with respect to the expression level of said same gene in at least one other clone tested in step a):
  i) upregulated, if the gene is a gene selected from the group of genes consisting of:
    ZdhhC6, Myrip, Actc1, AC124993.19, and Runx2, or
  ii) downregulated, if the gene is a gene selected from the group of genes consisting of: Fkbp10, AC158560.4, PlekhB1, Rps6KA2, Sept1, Sprr2k, and Flt1.

As mentioned previously, there may be more than two cell clones, e.g. the selection can be made in some embodiments from at least 3, 4, 5, 6, 7, 8, 9, 10, 15, 20, 50, 75 or at least 100 or more candidate clones. The selection of the respective clone in step b) is straightforward based on the respective expression level if only for one gene the expression level is determined. The "at least one other clone tested in step a)" may be the clone with the worst expression level among the clones tested for said gene. Consequently, the method of the present invention allows in principle to choose the second worst candidate. While choosing the second worst candidate clone may not seem to be the most logical choice, said choice is still better than choosing the clone with the worst expression levels. Moreover, the second worst candidate clone may still exhibit excellent expression level values. In other words, the present invention allows eliminating at least the worst choice. However, in most circumstances where more than two clones are analysed the person skilled in the art will usually not select the second worst candidate, but one of the best candidates if not the best candidate, i.e. the clone exhibiting the best expression level for the respective gene. In the latter scenario the selected clone does not only exhibit a better expression level vis-à-vis "one other clone tested in step a)", but vis-à-vis all other tested clones. In preferred embodiments, the selected clone exhibits a better expression level vis-à-vis 50% of all other tested clones (above mean), more preferably 75% of all other tested clones, more preferably vis-à-vis 80% of all other tested clones, more preferably vis-à-vis 85% of all other tested clones, more preferably vis-à-vis 90% of all other tested clones, more preferably vis-à-vis 95% of all other tested clones, most preferably a better expression level than all other tested clones. Preferably, a clone is selected, whose expression level differs from the (mean) expression level of the same gene in the at least one other clone by at least a two-fold change ($\log_2$).

In a particularly preferred embodiment of the invention the cell clones are CHO-K1 cell clones and the expression level of one or both genes selected from the group consisting of Fkbp10 and AC124993.19 are determined in the method according to the present invention. These genes have been proven to be particularly indicative for high producer clones in CHO-K1 cell clones.

In a further particularly preferred embodiment of the invention the cell clones are CHO-SSF3 cell clones and the expression level of one, two or all three genes selected from the group consisting of: Fkbp10, AC124993.19, and Runx2 are determined in the method according to the present invention. These genes have been proven to be particularly indicative for high producer clones in CHO-SSF3 cell clones.

In a further particularly preferred embodiment of the invention the cell clones are CHO-K1PD cell clones and the expression level of one, two, three or more than three or even all genes selected from the group consisting of: ZdhhC6, Myrip, Actc1, AC158560.4, PlekhB1, Rps6KA2, Sept1, Sprr2k, and Flt1 are determined in the method according to the present invention. These genes have been proven to be particularly indicative for high producer clones in CHO-K1PD cell clones.

As will be easily understood, the term "best expression level" (or "superior expression level") is a necessary relative term and its meaning will depend on the gene under scrutiny. For genes selected from the group consisting of ZdhhC6, Myrip, Actc1, AC124993.19 and Runx2 (upregulation group), a clone is selected exhibiting an upregulated (i.e. higher) expression level in comparison to the "at least one other clone tested in step a)". For genes selected from the group consisting of Fkbp10, AC158560.4, PlekhB1, Rps6KA2, Sept1, Sprr2k, and Flt1 (downregulation group), a clone is selected exhibiting an expression level which is downregulated (i.e. lower). For the upregulation group the value of the clone with the lowest expression value can be set as reference value and the results for the other clones may then be expressed as fold change (FC) vis-à-vis said expression value. For the downregulation group the value of the clone with the highest expression value can be set as reference value and the results for the other clones may then be expressed as fold change (FC) vis-à-vis said expression value.

As mentioned above, while determining the expression level of one gene selected from the group consisting of Fkbp10, ZdhhC6, Myrip, Actc1, AC124993.19, Runx2, AC158560.4, PlekhB1, Rps6KA2, Sept1, Sprr2k, and Flt1 is encompassed by the present invention, the present invention also contemplates determining the expression level of more than one gene. While in such scenario (more than one expression level determined) the subsequent selection decision can in principle be still based on only one of the determined expression levels (i.e. not all expression levels determined need to be taken into account), said selection decision will usually be made by taking into account the results for more than one gene. As long as the genes are from the same group of genes (upregulation group: ZdhhC6, Myrip, Actc1, AC124993.19 and Runx2; downregulation group: Fkbp10, AC158560.4, PlekhB1, Rps6KA2, Sept1, Sprr2k, and Flt1) the expression level results can be simply taken together. If the expression level of genes from both groups have been determined and are taken into consideration for the selection, then one must invert the algebraic sign for the values of one group, e.g. for the downregulation group (a -1.5 fold change in expression value (downregulation) is considered to be a (+) 1.5 FC), to allow combination of the expression values of the different groups. Eventually, a clone may be selected in such embodiments for further expansion, whose expression level taken together for said genes is superior to the level of said genes taken together in at least one other clone tested in step a).

As previously for one gene, if more than one gene is used as basis for the selection decision, the selected clone exhibits preferably a better expression level vis-à-vis 50% of all other tested clones (above mean), more preferably better expression level vis-à-vis 75% of all other tested clones, more preferably vis-à-vis 80% of all other tested clones, more preferably vis-à-vis 85% of all other tested clones, more preferably vis-à-vis 90% of all other tested clones, more preferably vis-à-vis 95% of all other tested clones, most preferably a better expression level than all other tested clones. Thus, in an embodiment of the invention, a clone may be selected in step b) for further expansion, whose expression level for said genes is superior to the mean expression level taken together for said genes, respectively, as determined for two or more other clones tested in step a). Preferably, a clone is selected, whose expression level differs from the (mean) expression levels of the same genes in the at least one other clone by at least a two-fold change ($\log_2$).

As previously discussed, the selection in step b) of the method of the invention is based on a comparison of the expression level (or levels) of the selected clone with at least one other clone tested in step a). The selected clone must exhibit a "superior" expression level for the respective genes (up-or downregulated, depending on the gene(s) analysed). However, the present invention also contemplates a selection of a clone on basis of an indirect comparison. In such scenario, a (first) clone may be selected indirectly on basis of a comparable or superior expression level for said gene (or expression levels taken together for said genes, respectively), as compared to at least one other clone tested in step a) (the second clone), provided that said at least one other clone (the second clone) has been previously verified to have a superior expression level for said gene (or expression levels taken together for said genes, respectively), as compared to at least one further clone (third clone) tested in step a). In other words, if previously an advantageous clone (the second clone) has already been identified (advantageous vis-à-vis the third clone), then the new (first) clone can be selected already on basis of a comparable (or superior) expression level vis-à-vis the second clone, because the new (first) clone will inevitably fulfill the criterion of having an advantageously up-or downregulated expression level for the respective gene or genes vis-à-vis the third clone.

The method according to the present invention is certainly not limited to selecting only one clone. Rather, more than one cell clone may be selected on basis of the prerequisites of step b) for further expansion.

Furthermore, the method of the present invention requires selecting out of said at least two cell clones a cell clone for "further expansion". As used herein, "for further expansion" is intended to specify that cell culturing of the respective clone is not discontinued. Rather, culturing of said clone is preferably continued until reliable productivity measurements can be made. Moreover, the clone is ideally even expanded (increase in cell number and/or culture volume) for large scale protein production.

The method of the present invention may therefore comprise the additional step of:

c) expanding said selected cell clone.

The method of the present invention is not practiced on the human or animal body, i.e. it is an ex vivo or in-vitro method, respectively, as will be readily understood by the person skilled in the art.

In a second aspect the present invention relates to a host cell for recombinant protein expression, the host cell exhibiting artificially modified gene expression of at least one gene selected from the group consisting of:

Fkbp10, ZdhhC6, Myrip, Actc1, AC124993.19, Runx2, AC158560.4, PlekhB1, Rps6KA2, Sept1, Sprr2k, and Flt1, wherein the gene expression is:

i) artificially upregulated, if the gene is a gene selected from the group of genes consisting of: ZdhhC6, Myrip, Actc1, AC124993.19, and Runx2, and/or ii) artificially downregulated, if the gene is a gene selected from the group of genes Fkbp10, AC158560.4, PlekhB1, Rps6KA2, Sept1, Sprr2k, and Flt1.

For instance, a host cell according to the present invention may exhibit artificially modified gene expression of at least one gene selected from the group of genes consisting of: ZdhhC6, Myrip, Actc1, AC124993.19 and Runx2, and the gene expression is artificially modified by overexpressing the respective gene or genes. Overexpression may be achieved by conventional means in the art, e.g. by (stable or transient) transfection with additional copies of said gene or by manipulation of respective regulatory means (e.g. change of promoter, removal of regulatory, e.g. inhibitory, sequences etc.). A host cell of the present invention may also exhibit artificially modified gene expression of at least one gene selected from the group consisting of Fkbp10, AC158560.4, PlekhB1, Rps6KA2, Sept1, Sprr2k, and Flt1, wherein the gene expression is artificially modified by decreasing or eliminating the expression of the respective gene or genes, e.g. by silencing, knockout or (transient or stable) knockdown of the respective gene or genes. In general, if gene expression for more than one gene is modified, then this may be achieved by the same means (e.g. all are knocked down, or by different means (e.g. one is knocked out, one is knocked down).

Preferably, the host cell is a mammalian host cell, such as human host cell or a rodent host cell. If the host cell is a mammalian cell, then said mammalian cell is preferably, but not necessarily, not a monkey cell, such as a COS cell. In particular such mammalian host cell is preferably not a monkey cell, such as a COS cell, if the host cell exhibits an artificially upregulated expression level of ZdhhC6. Particularly preferred host cells are CHO cells, such as CHO-K1 cells, CHO-SSF3 or CHO-K1PD cells. The host cell of the present invention is preferably an isolated host cell and thus not part of an intact higher organism.

The host cell of the invention is for recombinant protein expression but need not yet be transfected with the transgene encoding the recombinant protein. However, in some embodiments, the host cell comprises a transgene encoding a recombinant protein. The transgene may encode any type of recombinant protein. The recombinant protein may be for example an antibody, antibody light or heavy chain, a toxin, a cytokine, a growth factor, a growth factor receptor, an enzyme, or a hormone. Preferably, the recombinant protein is an antibody.

It is understood that embodiments discussed above for the inventive method also apply in the context of the inventive host cell, for instance with respect to the number of genes modified (e.g. at least 2, at least 3, at least 4, at least 5, at least 6, at least 7, at least 8, at least 9, at least 10, at least 11, or all 12 genes), preferred genes and groups of genes per cell line etc.

The term "comprising", as used herein, shall not be construed as being limited to the meaning of "consisting of" (i.e. excluding the presence of additional other matter). Rather, "comprising" implies that optionally additional matter, features or steps may be present. The term "comprising" encompasses as particularly envisioned embodiments falling within its scope "consisting of" (i.e. excluding the presence of additional other matter) and "comprising but not consisting of" (i.e. requiring the presence of additional other matter, features or steps), with the former being more preferred.

The use of the word "a" or "an", when used herein, may mean "one," but it is also consistent with the meaning of "one or more," "at least one," and "one or more than one." In particular, "determining . . . the expression level of a gene" selected from the inventive group does not preclude determining the expression level of another gene from said group or of other genes not within this group. Likewise, "selecting a cell clone" may refer to selecting only one cell clone, but does not exclude selecting more than one cell clone.

"A suitable candidate cell clone", as used herein, will be preferably a cell clone yielding a titre of ≥300 μg/ml of recombinant protein such as an antibody.

EXAMPLES

In the following, specific examples illustrating various embodiments and aspects of the invention are presented. However, the present invention shall not to be limited in scope by the specific embodiments described herein. Indeed, various modifications of the invention in addition to those described herein will become readily apparent to those skilled in the art from the foregoing description, accompanying figures and the examples below. All such modifications fall within the scope of the appended claims.

Example 1

General Outline of the Experiment

The inventors of the present invention have established a transcriptome profile of recombinant CHO cell clones. The transcriptome profiles of 3 different CHO cell line derivatives were established. Based on the titre results, the clones were categorized in two groups; high (titre >300 ug/ml) and low (<200 ug/ml) producing clones. The clones were cultivated in animal component free medium in suspension mode (shaking flasks). Simple 10-day batch was performed for all clones and titre was measured on day 10. Total RNA was isolated from each clone and used for transcriptome profiling by DNA microarrays and reverse transcription-quantitive PCR (RT-qPCR). The transcript profile of high and low producing clones was performed using DNA microarrays with 61,223 probes. The number of transcripts was reduced to top 12 differentially expressed genes which were selected for further verification using RT-qPCR method.

Figure 1:
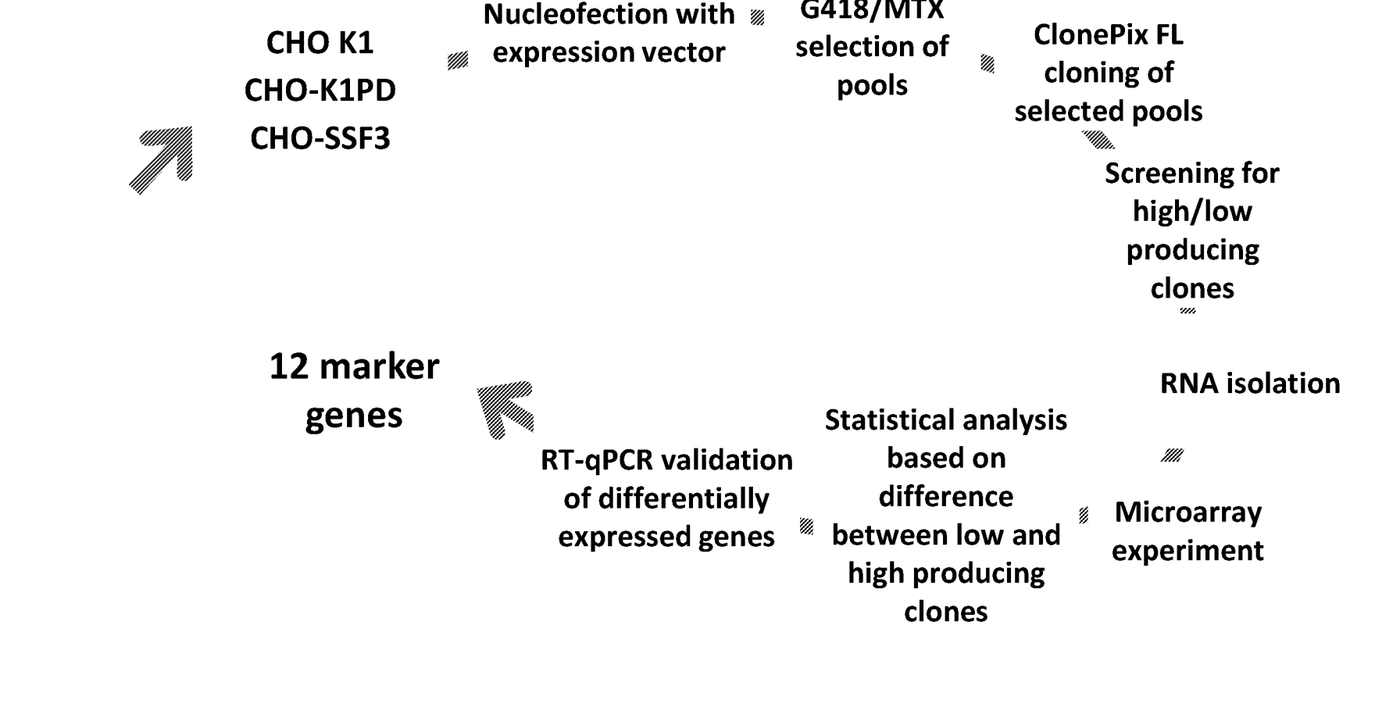
FIG. 1: gives a schematic overview regarding the set-up of the experiment.

By comparing the transcriptome profile between 28 high and low producing clones, originating from 3 different cell lines, the inventors have identified 12 genes which are significantly differentially expressed between high and low producing clones. An overview of the experiment is illustrated in FIG. 1. The transcriptome (microarray analysis, verification with RT-qPCR) comparison between high and low producing clones yielded the following 12 genes: ZdhhC6, Myrip, Actc1, AC124993.19, Runx2, AC158560.4, PlekhB1, Rps6KA2, Sept1, Sprr2k, Flt1, and Fkbp10.

Example 2

Cell Culture

Cell Line Selection

The original CHO cell line was spontaneously isolated from a female Chinese hamster (*Cricetulus griseus*) already in 1957. A proline dependent strain (CHO-K1) was derived from the original cell line, which is the source of all parental cell lines used in the present study: CHO-K1, CHO-K1PD and CHO-SSF3.

Cell lines were cultured in serum free media (Irvine Scientific), supplemented with L-glutamine (Sigma).

Expression Vector, Nucleofection and Pool Generation

An expression vector was constructed encoding a light (Lc) and heavy chain (Hc) of a monoclonal antibody (mAb), an antibiotic resistance gene and a dihydrofolate reductase (Dhfr) gene. To produce transfection pools cell lines were transfected with linearized expression vector using the nucleofection method (Nucleofector, Lonza) according to the manufacturer's protocol. After transfection, antibiotic selection using geneticin (G418) was performed, followed by amplification of the transgene by methotrexate (MTX).

Cloning and Titer Determination

Cloning of selected pools was performed using ClonePix FL technology (Molecular Devices). Good growing culture (in exponential growth phase with cell viability above 90%) was seeded into 6-well microtiter plates at low seeding density in semi-solid media composed of methylcellulose and concentrated basal animal component free medium. Clonal colonies formed in viscose nature of semi-solid medium were transferred into 96-well plates filled with liquid medium. Clones were further expanded into two parallel shake flasks. One parallel was used to prepare the cell material for nucleic acid extraction (RNA/DNA). Cells were collected at the early exponential growth phase (after 72 hours). The second shake flask was used to perform 10-day simple batch in order to measure productivity (titre). Titres were measured using Octet QK system (ForteBio) and clones were classified into two productivity groups (L—Low, H—High).

Example 3

DNA Microarrays

RNA Isolation

The samples for RNA isolation were taken on day 3 (early log growth phase) after the passage. Total RNA was isolated by automated QiaCube (Qiagen) system using Rneasy Mini Kit (Qiagen), following the manufacturers protocol. RNA was examined by ND-1000 Spectrophotometer (NanoDrop Technologies) and RNA integrity was checked by Agilent RNA Nano chip on Bioanalyzer 2100 (Agilent).

Hybridization

Before hybridization to the proprietary CHO specific DNA microarrays V3 (manufactured by Affymetrix) all mRNA samples were diluted appropriately to the same concentration. Biotinylated cRNA was prepared according to the protocol described in the Affymetrix technical manual. The expression DNA microarray consist of 61,223 probe sets, targeting approximately 26,227 Chinese hamster unique gene IDs and 14,657 unique Ensembl mouse genes. cRNA was synthesized from cDNA using the 3'-IVT Express kit (Affymetrix). Subsequent hybridization onto the custom microarray was performed in the GeneChip Hybridization Oven 640 (Affymetrix) and the processing was done using the GeneChip Fluidics Station 450 (Affymetrix).

Statistical Analysis of DNA Microarray Data

The raw image files were processed using the GeneSpring GX software (Agilent Technologies) and normalized using the robust multichip average algorithm (RMA). Further statistical analysis to identify differentially expressed genes was performed using statistical software R.

Example 4

Reverse Transcription Quantitative Real-Time PCR (RT-qPCR)

4.1 Gene Expression

RNA Isolation, DNAseI Reaction and RT Reaction

The same total RNA was used for reverse transcription quantitative PCR (RT-qPCR) analysis as it was used for DNA microarrays. An additional step of genomic DNA removal using Dnase I (Ambion) was performed prior to cDNA synthesis. DNaseI was added to 5 µg of total RNA and incubated (25 min at 37° C., 10 min at 75° C.). After DNase treatment RNA was transcribed into cDNA.

Sample Preparation for Gene Expression (RT-qPCR)

Twelve differentially expressed genes from the microarray data were groundwork for further verification using RT-qPCR.

TaqMan-MGB® probes were for all genes designed and manufactured at Life Technologies. All qRT-PCR reactions were performed on an ABI PRISM® 7900 Sequence Detection System (Life Technologies) in 384-well plate format using universal cycling conditions (2 min at 50° C., 10 min at 95° C., followed by 45 cycles of 15 s at 95° C. and 1 min at 60° C.) which allowed all reactions to be run on the same plate. Real-time PCR was performed in a final reaction volume of 10 µL containing 2 µL of sample cDNA, 900 nm of each primer, 250 nm of probe and 1x TaqMan® PCR Master Mix (Life Technologies), which includes ROX™ as a passive reference dye. Each sample DNA was tested with: 12 target genes and two endogenous controls (ACTB, GAPDH). Each reaction was performed in three replicate wells in two dilutions on the same 384-well plate. QIAgility automated liquid handling system (Qiagen) was used to prepare cDNA dilutions and to pipette large numbers of cDNA samples and master mixes onto the 384-well plates.

Statistical Analysis

The dilution factors were determined individually for each amplicon on a subset of samples, in order for the quantification cycle (Cq) values to be in the range 22—34. The software SDS 2.1 (Life Technologies) was used for fluorescence acquisition and Cq calculation. For this calculation, the baseline was set automatically and the fluorescence threshold set manually (0.1) to intersect with the linear part of the amplification curves of all amplicons in all runs. The relative quantification approach was used (Pfaffl, M. W., Nucleic Acids Res, 2001. 29(9): p. e45). Each sample was analysed in two dilutions and three replicates per dilution step. Only samples where the ΔCq between two dilutions of target gene did not deviate by more than 0.5 from ΔCt of the reference gene were used for relative quantification. Additionally, the ΔCq values between the two dilutions of cDNA were calculated for each sample and used to calculate approximate amplification efficiencies ($E=10[1/\Delta Cq]$) for each sample individually. These sample-specific efficiencies were used in the relative quantification formula.

The geometric mean of Cq values of separate reference gene was used as the final reference (Vandesompele, J., et al., Genome Biol, 2002. 3(7): p. RESEARCH0034). A relative expression ratio was calculated separately for each dilution of each sample and averaged to yield the final relative expression ratio for the sample (Pfaffl, M. W., Nucleic Acids Res, 2001. 29(9): p. e45). The ratio was then $\log_e$ transformed. All mathematical operations were performed in Microsoft Excel (Microsoft).

The Welch two tailed t-test was used to determine statistically significant differences between relative expression ratios of high and low producing clones with a p-value<0.05 as the limit for statistical significance.

4.2 Transgene Copy Number

Additionally, genomic DNA (gDNA) was isolated from all analysed clones using QlAamp DNA Blood Mini Kit (Qiagen). Quantitative real time PCR (qPCR) was performed to confirm the presence of gene for Light (Lc) and Heavy chain (Hc) transfected into cell lines.

DNA Isolation

The genomic DNA (gDNA) from all clones was isolated using DNA Blood Kit (Qiagen) with automated system for DNA isolation (QiaCube, Qiagen), according to the manufacturer's protocol. gDNA was quantified by ND-1000 Spectrophotometer (NanoDrop Technologies).

Copy Number

Copy number of light chain (Lc) and heavy chain (Hc) were determined by qPCR (ABI PRISM 7900, Applied Biosystems/Life Technologise) on all samples. Q1Agility automated liquid handling system (Qiagen) was used to prepare DNA dilutions and to pipette large numbers of DNA samples and master mixes onto the 384-well plates. TaqMan-MGB® probes for all 12 genes were designed and manufactured at Life Technologies. Each 10 µl reaction comprises 2 µl of DNA (10 ng/µl), 5 µl 2× master mix (Applied Biosystems), 2 µl of nuclease free water, 1 µl of 10× gene specific primer-probe mix. Primer-probe mix were designed and manufactured at Life Technologies. All reactions were performed in triplicates. Cycling parameters were 48° C. for 2 min, 95° C. for 10 min, followed by 40 cycles 95° C. for 15 s, and 60° C. for 1 min Data Analysis Copy number of Lc and Hc was calculated using absolute quantification method. Standard curve was constructed by using the DNA of the same expression vector, as it was used for transfection of host cell line and gDNA of parental host cell line. The software SDS 2.1 (Life Technologies) was used for fluorescence acquisition and Cq calculation. Copy numbers of Lc/Hc and gluc in the sample were extrapolated from the standard curves. The ratio between endogenous gene Gluc (single copy gene) and Lc/Hc was calculated for determination of the Lc/Hc copy number per cell.

Example 5

Results

Based on titre results clones were separated into two productivity groups:
Low producing clones with titre below 200 mg/L
High producing clones with titre above 300 mg/L All clones selected for the analysis were confirmed to contain intact Lc and Hc of gene of interest transfected into cell lines. Lc and Hc presence was confirmed and copy number of LC and HC determined for all samples based on genomic DNA using qPCR.

Based on statistical significance the expression of 12 genes ($\log_2$ FC>1 in both directions, $p_{adj}$-value<0.05) were verified with RT-qPCR method. 12 genes were identified as differentially expressed in high versus low producing clones: AC158560.4, PlekhB1, Rps6KA2, Sept1, Sprr2k, Flt1, Fkbp10, ZdhhC6, Myrip, Actc1, AC124993.19 and Runx2.

Genes AC158560.4, PlekhB1, Rps6KA2, Sept1, Sprr2k, Flt1 and Fkbp10 were down-regulated in high producing clones. Among these, 6 genes (AC158560.4, PlekhB1, Rps6KA2, Sept1, Sprr2k, Flt1) were identified as particularly useful marker genes for productivity in CHO-K1PD cell line. The down-regulated gene Fkbp10 was identified to be particularly useful for predicting the productivity in CHO-K1 and CHO-SSF3 cells. Table 2 below illustrates per cell line the most useful marker genes, which are down-regulated in high producing clones.

TABLE 2

| | | Cell line | | | | | | | |
|---|---|---|---|---|---|---|---|---|---|
| | | CHO-K1PD | | | | | | CHO-K1 | CHO-SSF3 |
| | | Gene name | | | | | | | |
| | | AC158560.4 | PlekhB1 | Rps6KA2 | Sept1 | Sprr2k | Flt1 | Fkbp10 | Fkbp10 |
| Average expression values ($\log_2$) | High producing clones (expression values-$\log_2$) | 6.31 | 8.68 | 9.07 | 7.1 | 9.05 | 4.39 | −0.25 | −0.72 |
| | Low producing clones (expression values-$\log_2$) | 8.34 | 9.72 | 10.12 | 8.12 | 10.06 | 6.35 | 1.25 | 0.37 |
| Stdev | High producing clones (expression values-$\log_2$) | 1.14 | 0.63 | 0.49 | 0.43 | 0.4 | 0.93 | 0.33 | 0.29 |
| | Low producing clones (expression values-$\log_2$) | 1.7 | 0.89 | 0.68 | 1.04 | 0.72 | 0.88 | 0.46 | 0.63 |
| Difference in expression values ($\log_2$) – High vs Low producing clones | | −2.03 | −1.05 | −1.05 | −1.02 | −1.01 | −1.96 | −1.50 | −1.09 |
| $p_{adj}$ - value | | 0.0001 | 0.0013 | 5.20E−05 | 0.0012 | 1.75E−05 | 7.90E−08 | 0.0132 | 0.0142 |

Further on, five genes ZdhhC6, Myrip, Actc1, AC124993.19 and Runx2 were all up-regulated in high producing clones. Genes ZdhhC6, Myrip and Actc1 were identified as particularly useful marker genes for productivity in CHO-K1PD cell lines. Gene AC124993.19 was identified to be particularly useful for predicting the productivity in CHO-K1 cells. Genes AC124993.19 and Runx2 were identified as being the most useful marker genes in predicting productivity for CHO-SSF3 cells. Table 3 below illustrates per cell line the most useful marker genes, which are up-regulated in high producing clones.

TABLE 3

| | | Cell line | | | | |
|---|---|---|---|---|---|---|
| | | CHO-K1PD | | CHO-K1 | CHO-SSF3 | |
| | | | | Gene name | | |
| | | ZdhhC6 | Myrip | Actc1 | AC124993.19 | AC124993.19 | Runx2 |
| Average expression values (log$_2$) | High producing clones (expression values-log$_2$) | 8.73 | 6.58 | −2.18 | −1.52 | 0.90 | 0.91 |
| | Low producing clones (expression values-log$_2$) | 7.64 | 3.97 | −5.09 | −5.20 | −0.41 | −0.26 |
| Stdev | High producing clones (expression values-log$_2$) | 0.45 | 1.33 | 1.72 | 2.93 | 0.62 | 0.57 |
| | Low producing clones (expression values-log$_2$) | 0.58 | 2.07 | 1.08 | 1.43 | 0.32 | 0.45 |
| Difference in expression value (log$_2$) – High vs Low producing clones | | 1.09 | 2.61 | 2.91 | 3.68 | 1.31 | 1.17 |
| p$_{adj}$ - value | | 7.95E−08 | 0.0004 | 0.0148 | 0.0500 | 0.0055 | 0.0079 |

The Welch two tailed t-test was used to determine statistically significant differences between relative expression ratios of high and low producing clones with a p$_{adj}$-value<0.05 as the limit for statistical significance.

Both Tables 2 and 3 show log$_2$ FC expression values for high and low producing group of clones separately, which is the basis for fold change (FC) expression value calculation comparing high vs. low producing clones. The threshold for the difference (FC) between expression values (log$_2$) in high versus low producing clones was minimum log$_2$ FC>=1 or log$_2$ FC<=−1 for assuring more significant results. A p$_{adj}$-value is significantly lower in all genes than normally used threshold of 0.05 in biological samples.

Example 6

CRISPR/CAS9 Experiment

CRISPR (Clustered Regularly Interspaced Short Palindromic Repeats) is used in the art as RNA guided genome editing tool. The CRISPR system was discovered in bacteria where it acts as bacterial immune system to defend against invading viruses. The technology has been routinely used in the art to functionally inactivate genes in cells, to overexpress genes of interest in cells or for exchanging/swapping genes in cells.

The purpose of the experiment was to further verify the importance of the expression level of the genes identified previously as being relevant for high recombinant protein production. In this experiment, those genes were analysed which had been shown to be downregulated in high producing clones. This was done by using the CRISPR/CAS9 genome editing tool targeting 6 of the identified marker genes: PlekhB1, Rps6KA2, Sept1, Sprr2k, Flt1, and Fkbp10. A similar experiment can be done for AC158560.4.

Clones already producing recombinant protein were co-transfected with a vector containing puromycin resistance and the specific nucleotide sequence targeting marker gene (CRISPR). 3 clones (previously identified as high producing clones) were transfected with the "CRISPR vector". In parallel a control was used for each clone lacking transfection with the "CRISPR vector". After transfection puromycin was used for selection purpose and afterwards 10-day simple batch cultivation was performed. Then the titre of recombinant protein was measured.

For all 6 genes tested in the 3 original clones (K10, K17, K20), the productivity was higher after treatment with "CRISPR vectors" targeting the individual genes as compared to the control (i.e. w/o any CRISPR vector) (see table 4). In other words, the productivity in high producing clones could even be further improved by additional silencing of genes identified in the present invention as important for high recombinant protein production when downregulated.

TABLE 4

Recombinant protein titre for three clones and six genes after CRISPR/CAS9 experiment

| Clone | Knock out gene | Clone No. | Titre [mg/L] |
|---|---|---|---|
| K10 | control | K10 | 510.1 |
| | PlekhB1 | K10_P1 | 679.9 |
| | Rps6KA2 | K10_P2 | 717.1 |
| | Sept1 | K10_P3 | 609.1 |
| | Sprr2k | K10_P4 | 728.6 |
| | Flt1 | K10_P5 | 729 |
| | Fkbp10 | K10_P6 | 647.3 |
| K17 | control | K17 | 513.5 |
| | PlekhB1 | K17_P1 | 716.9 |
| | Rps6KA2 | K17_P2 | 691 |
| | Sept1 | K17_P3 | 722.2 |

TABLE 4-continued

Recombinant protein titre for three clones and six genes after CRISPR/CAS9 experiment

| Clone | Knock out gene | Clone No. | Titre [mg/L] |
|---|---|---|---|
|  | Sprr2k | K17_P4 | 721.9 |
|  | Flt1 | K17_P5 | 741.1 |
|  | Fkbp10 | K17_P6 | 666.5 |
| K20 | control | K20 | 427.9 |
|  | PlekhB1 | K20_P1 | 707.9 |
|  | Rps6KA2 | K20_P2 | 654.8 |
|  | Sept1 | K20_P3 | 650.2 |
|  | Sprr2k | K20_P4 | 716.5 |
|  | Flt1 | K20_P5 | 618 |
|  | Fkbp10 | K20_P6 | 540.5 |

It is also conceivable to use the CRISPR tool in a later experiment for studying in more detail the marker genes shown to be upregulated in high producing clones, i.e. ZdhhC6, Myrip, Actc1, AC24993.19 and Runx2.

The invention claimed is:

1. Method for selecting a suitable candidate cell clone for recombinant protein expression, the method comprising the steps of:
   a) determining for at least two cell clones the RNA expression level of a marker gene selected from the group consisting of:
      FK506 binding protein 10 gene (Fkbp10), zinc finger, DHHC domain containing 6 Gene (ZdhhC6), myosin VIIA and Rab interacting protein gene (Myrip), actin, alpha, cardiac muscle 1 gene (Actc1), AC124993.19, runt related transcription factor 2 gene (Runx2), AC158560.4, pleckstrin homology domain containing, family B (evectins) member 1 gene (PlekhB1), ribosomal protein S6 kinase, polypeptide 2 gene (Rps6KA2), septin 1 gene (Sept1), small proline-rich protein 2K gene (Sprr2k), and FMS-like tyrosine kinase 1 gene (Flt1), and
   b) selecting out of said at least two cell clones a cell clone for further expansion, whose RNA expression level of said gene is with respect to the expression level of said same gene in at least one other clone tested in step a):
      i) upregulated, if the gene is a gene selected from the group of genes consisting of: ZdhhC6, Myrip, Actc1, AC124993.19 and Runx2, or
      ii) downregulated, if the gene is selected from the group of genes consisting of: Fkbp10, AC158560.4, PlekhB1, Rps6KA2, Sept1, Sprr2k, and Flt1.

2. The method according to claim 1, wherein the at least two cell clones express a recombinant protein.

3. The method according to claim 1, wherein the expression level of more than one gene selected from the group consisting of:
   Fkbp10, ZdhhC6, Myrip, Actc1, AC124993.19, Runx2, AC158560.4, PlekhB1, Rps6KA2, Sept1, Sprr2k, and Flt1
is determined, and wherein a clone is selected for further expansion, whose expression level taken together for said genes is lower than the expression level of said genes taken together in at least one other clone tested in step a).

4. The method according to claim 1, wherein a clone is selected in step b) for further expansion, whose expression level for said gene or expression levels taken together for said genes, respectively, is lower than the mean expression level for said gene or mean expression level taken together for said genes, respectively, as determined for two or more other clones tested in step a).

5. The method according to claim 1, wherein the clone is selected in step b) on basis of a comparable or lower expression level for said gene or expression level taken together for said genes, respectively, as compared to at least one second clone tested in step a),
   wherein, if only one gene is tested in step a), said at least one second clone exhibits an expression level of said gene, which is with respect to the expression level of said same gene in at least one other clone tested in step a):
      i) upregulated, if the gene is a gene selected from the group of genes consisting of: ZdhhC6, Myrip, Actc1, AC124993.19 and Runx2, or
      ii) downregulated, if the gene is a gene selected from the group of genes consisting of: Fkbp10, AC158560.4, PlekhB1, Rps6KA2, Sept1, Sprr2k, and Flt1, or
   wherein, if more than one gene is tested in step a), said at least one second clone exhibits an expression level taken together for said genes which is lower than the expression level of said genes taken together in at least one further clone tested in step a).

6. The method according to claim 1, wherein the method further comprises the step of:
   c) expanding said selected cell clone.

7. The method according to claim 1, wherein the cell clones are Chinese hamster ovary (CHO) cell clones.

8. The method according to claim 1, wherein the cell clones are CHO-K1 cell clones and the gene or genes are selected from the group consisting of: Fkbp10 and AC124993.19.

9. The method according to claim 1, wherein the cell clones are CHO-SSF3 cell clones and the gene or genes are selected from the group consisting of:
   Fkbp10, AC124993.19, and Runx2.

10. The method according to claim 1, wherein the cell clones are CHO-K1PD cell clones and the gene or genes are selected from the group consisting of: ZdhhC6, Myrip, Actc1, AC158560.4, PlekhB1, Rps6KA2, Sept1, Sprr2k, and Flt1.

11. The method according to claim 1, wherein a recombinant protein expressed by said clones is an antibody.

12. The method according to claim 1, wherein determining the expression level in step a) involves quantitative RT-PCR.

* * * * *

SEQUENCE LISTING

<160> NUMBER OF SEQ ID NOS: 36

<210> SEQ ID NO 1
<211> LENGTH: 29
<212> TYPE: DNA
<213> ORGANISM: Cricetulus griseus

<400> SEQUENCE: 1
gcattcaatt taatttgcca agtcaggaa                                29

<210> SEQ ID NO 2
<211> LENGTH: 25
<212> TYPE: DNA
<213> ORGANISM: Cricetulus griseus

<400> SEQUENCE: 2
ccttcttccc actactagct tctct                                    25

<210> SEQ ID NO 3
<211> LENGTH: 27
<212> TYPE: DNA
<213> ORGANISM: Cricetulus griseus

<400> SEQUENCE: 3
tgtgctatct aatgttggca gtattgt                                  27

<210> SEQ ID NO 4
<211> LENGTH: 15
<212> TYPE: DNA
<213> ORGANISM: Cricetulus griseus

<400> SEQUENCE: 4
ctgcgccgca tgcaa                                               15

<210> SEQ ID NO 5
<211> LENGTH: 24
<212> TYPE: DNA
<213> ORGANISM: Cricetulus griseus

<400> SEQUENCE: 5
ctctcatgga tgccgaagaa tctt                                     24

<210> SEQ ID NO 6
<211> LENGTH: 19
<212> TYPE: DNA
<213> ORGANISM: Cricetulus griseus

<400> SEQUENCE: 6
ctttgtgcag tgccttgct                                           19

<210> SEQ ID NO 7
<211> LENGTH: 24
<212> TYPE: DNA
<213> ORGANISM: Cricetulus griseus

<400> SEQUENCE: 7
gcctgtttga agacatggat ctca                                          24

<210> SEQ ID NO 8
<211> LENGTH: 20
<212> TYPE: DNA
<213> ORGANISM: Cricetulus griseus

<400> SEQUENCE: 8
caggcccatc cattgtccat                                               20

<210> SEQ ID NO 9
<211> LENGTH: 22
<212> TYPE: DNA
<213> ORGANISM: Cricetulus griseus

<400> SEQUENCE: 9
gctctccttt gggtggaaca cc                                            22

<210> SEQ ID NO 10
<211> LENGTH: 25
<212> TYPE: DNA
<213> ORGANISM: Cricetulus griseus

<400> SEQUENCE: 10
gcctgttcta tggcatttga acttt                                         25

<210> SEQ ID NO 11
<211> LENGTH: 21
<212> TYPE: DNA
<213> ORGANISM: Cricetulus griseus

<400> SEQUENCE: 11
cgcccatctc agcttcttca a                                             21

<210> SEQ ID NO 12
<211> LENGTH: 38
<212> TYPE: DNA
<213> ORGANISM: Cricetulus griseus

<400> SEQUENCE: 12
cttttgtttt tatttcttat ttttctgatt gctattgc                           38

<210> SEQ ID NO 13
<211> LENGTH: 31
<212> TYPE: DNA
<213> ORGANISM: Cricetulus griseus

<400> SEQUENCE: 13
cgcatggaat ttcaaaaaat tgaaaagttg t                                  31

<210> SEQ ID NO 14
<211> LENGTH: 20
<212> TYPE: DNA
<213> ORGANISM: Cricetulus griseus

<400> SEQUENCE: 14

```
gctcacctga tccacagcaa                                                  20

<210> SEQ ID NO 15
<211> LENGTH: 26
<212> TYPE: DNA
<213> ORGANISM: Cricetulus griseus

<400> SEQUENCE: 15
tggcatattt tcttctgtgc ttgaga                                           26

<210> SEQ ID NO 16
<211> LENGTH: 18
<212> TYPE: DNA
<213> ORGANISM: Cricetulus griseus

<400> SEQUENCE: 16
gccctgagcc tggttctg                                                    18

<210> SEQ ID NO 17
<211> LENGTH: 25
<212> TYPE: DNA
<213> ORGANISM: Cricetulus griseus

<400> SEQUENCE: 17
ctcatggaaa tgccttccct agtaa                                            25

<210> SEQ ID NO 18
<211> LENGTH: 19
<212> TYPE: DNA
<213> ORGANISM: Cricetulus griseus

<400> SEQUENCE: 18
tgccgtcttc gggtaatgc                                                   19

<210> SEQ ID NO 19
<211> LENGTH: 22
<212> TYPE: DNA
<213> ORGANISM: Cricetulus griseus

<400> SEQUENCE: 19
gtcctttgcc ctcattcact tg                                               22

<210> SEQ ID NO 20
<211> LENGTH: 25
<212> TYPE: DNA
<213> ORGANISM: Cricetulus griseus

<400> SEQUENCE: 20
gcacaatacc accatcctga atgta                                            25

<210> SEQ ID NO 21
<211> LENGTH: 25
<212> TYPE: DNA
<213> ORGANISM: Cricetulus griseus

<400> SEQUENCE: 21
gaatggaatg attgggagag gatct                                            25

<210> SEQ ID NO 22
<211> LENGTH: 41
<212> TYPE: DNA
<213> ORGANISM: Cricetulus griseus

<400> SEQUENCE: 22
```
aaaataattt tctggaacta tagcatgttt atggtttaaa t        41

<210> SEQ ID NO 23
<211> LENGTH: 26
<212> TYPE: DNA
<213> ORGANISM: Cricetulus griseus

<400> SEQUENCE: 23
atgataaacc tactcccctc tttcca        26

<210> SEQ ID NO 24
<211> LENGTH: 25
<212> TYPE: DNA
<213> ORGANISM: Cricetulus griseus

<400> SEQUENCE: 24
tgacctgtgg tacaaagcag aattt        25

<210> SEQ ID NO 25
<211> LENGTH: 15
<212> TYPE: DNA
<213> ORGANISM: Cricetulus griseus

<400> SEQUENCE: 25
cctcctggaa cctcc        15

<210> SEQ ID NO 26
<211> LENGTH: 16
<212> TYPE: DNA
<213> ORGANISM: Cricetulus griseus

<400> SEQUENCE: 26
caatccctgg gtttcc        16

<210> SEQ ID NO 27
<211> LENGTH: 16
<212> TYPE: DNA
<213> ORGANISM: Cricetulus griseus

<400> SEQUENCE: 27
caacgcaggc atctta        16

<210> SEQ ID NO 28
<211> LENGTH: 16
<212> TYPE: DNA
<213> ORGANISM: Cricetulus griseus

<400> SEQUENCE: 28
ctgagcttgc atcttc        16

<210> SEQ ID NO 29
<211> LENGTH: 14
<212> TYPE: DNA
<213> ORGANISM: Cricetulus griseus

<400> SEQUENCE: 29
acaccccaaa tgcc        14

<210> SEQ ID NO 30
<211> LENGTH: 16
<212> TYPE: DNA
<213> ORGANISM: Cricetulus griseus

```
<400> SEQUENCE: 30
ccccgcctat acatca                                             16

<210> SEQ ID NO 31
<211> LENGTH: 16
<212> TYPE: DNA
<213> ORGANISM: Cricetulus griseus

<400> SEQUENCE: 31
cccagaagag ttctcc                                             16

<210> SEQ ID NO 32
<211> LENGTH: 19
<212> TYPE: DNA
<213> ORGANISM: Cricetulus griseus

<400> SEQUENCE: 32
caagtgcttc taagatgtc                                          19

<210> SEQ ID NO 33
<211> LENGTH: 15
<212> TYPE: DNA
<213> ORGANISM: Cricetulus griseus

<400> SEQUENCE: 33
ccgggctgca ctcat                                              15

<210> SEQ ID NO 34
<211> LENGTH: 16
<212> TYPE: DNA
<213> ORGANISM: Cricetulus griseus

<400> SEQUENCE: 34
ccttgtgcca aataag                                             16

<210> SEQ ID NO 35
<211> LENGTH: 17
<212> TYPE: DNA
<213> ORGANISM: Cricetulus griseus

<400> SEQUENCE: 35
catctcacag aaaactc                                            17

<210> SEQ ID NO 36
<211> LENGTH: 17
<212> TYPE: DNA
<213> ORGANISM: Cricetulus griseus

<400> SEQUENCE: 36
catggaaagc aaacctt                                            17
```